United States Patent [19]

Rosenblum

[11] 4,175,426
[45] Nov. 27, 1979

[54] APPARATUS FOR MEASURING THE SEDIMENTATION CHARACTERISTICS OF PARTICULATE SOLIDS IN LIQUID

[75] Inventor: Frank R. Rosenblum, Ville St. Laurent, Canada

[73] Assignee: Noranda Mines Limited, Toronto, Canada

[21] Appl. No.: 940,321

[22] Filed: Sep. 7, 1978

[30] Foreign Application Priority Data

Apr. 24, 1978 [CA] Canada .................................. 301784

[51] Int. Cl.² .......................................... G01N 15/04
[52] U.S. Cl. ...................................... 73/61.4; 73/438
[58] Field of Search ...................... 73/61.4, 61 R, 438, 73/432 PS

[56] References Cited

U.S. PATENT DOCUMENTS

| 2,371,457 | 3/1945 | Mendius ................................. 73/438 |
| 3,554,010 | 1/1971 | Van der Veen et al. ........... 73/61 R |
| 3,788,146 | 1/1974 | Hartman .......................... 73/61.4 X |
| 3,896,660 | 7/1975 | Valentyik ............................. 73/61.4 |

FOREIGN PATENT DOCUMENTS 375525  6/1973  U.S.S.R. .................................. 73/61.4

Primary Examiner—Charles A. Ruehl
Assistant Examiner—Joseph W. Roskos
Attorney, Agent, or Firm—Fleit & Jacobson

[57] ABSTRACT

An apparatus for measuring the sedimentation characteristics of particulate solids in liquid is disclosed. The apparatus comprises two separate vertical housings adapted to be filled to the same level with a liquid less dense than the particulate solids to be measured, means for introducing a sample of particulate solids to be measured in one of the housings, two pressure sensors located at the same level, one in each housing, and a differential pressure transducer connected to such pressure sensors for sensing the differential pressure caused by the sample introduced into one of the housings. The differential pressure transducer provides an output indicative of the weight percent of sample remaining in suspension as a function of time and such output may be used to determine the weight fraction of the particulate solids passing any given mesh size, or for measuring the specific gravity of particulate material of known dry weight.

10 Claims, 7 Drawing Figures

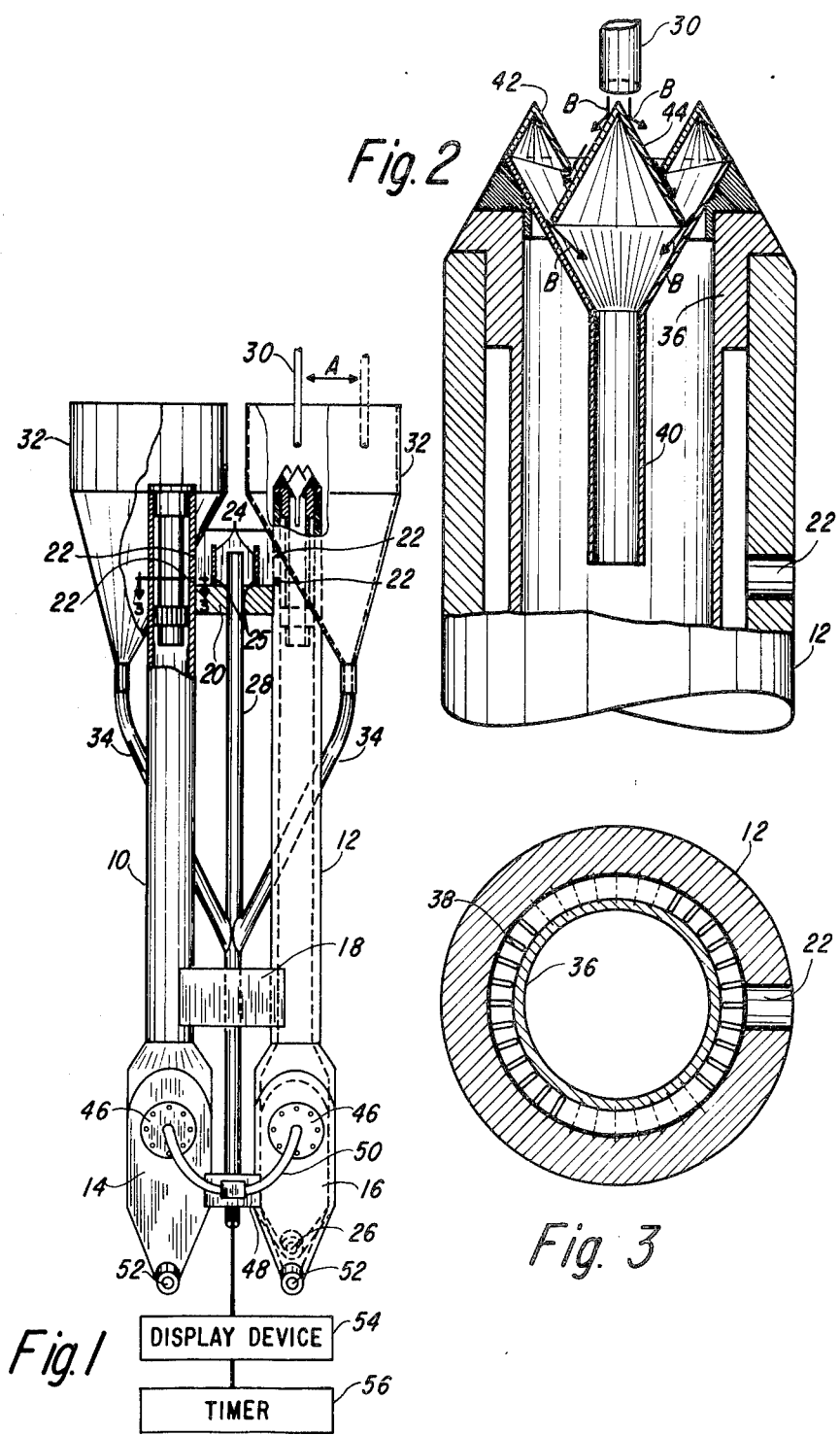

APPARATUS FOR MEASURING THE SEDIMENTATION CHARACTERISTICS OF PARTICULATE SOLIDS IN LIQUID

This invention relates to an apparatus for measuring the sedimentation characteristics of particulate solids in liquid and, more particularly, to an apparatus for determining the weight fraction of such particulate solids passing any given mesh size, or for measuring the specific gravity of particulate solids from the sedimentation data.

An apparatus for measuring the sedimentation characteristics of particulate solids is disclosed in U.S. Pat. No. 3,896,660 issued July 29, 1975. The apparatus uses a plurality of vertically spaced pressure sensors located in a sedimentation tube. The vertically spaced pressure sensors are connected to a transducer for sensing the hydrostatic pressure exerted on the pressure sensors by a suspension of solid particles in a liquid contained in such sedimentation tube. However, the above apparatus uses a single sedimentation tube and thus senses the absolute pressure created by the solid particles in suspension. The sensitivity of such an apparatus is low because the weight of the column of liquid in the sedimentation tube is also measured and it must be substracted from the readings of the pressure transducer in order to get a useful result. Furthermore, the above apparatus permits measurement of the sedimentation characteristics of dry solid particles only as any water added with the solid particles would affect the readings. The apparatus disclosed in the above patent also uses liquid as the pressure transmitting medium between the sensors and the transducer and filter discs to prevent the solids from getting to the transducer. The filter discs could plug up and render the apparatus non-usable.

It is therefore the object of the present invention to provide a sedimentation apparatus which is free of the short-comings of the previous sedimentation devices.

The apparatus, in accordance with the invention, comprises two separate vertical housings adapted to be filled to the same level with a liquid less dense than the particulate solids to be measured, means for introducing a sample of particulate solids to be measured in one of the housings, two pressure sensors located at the same level, one in each housing, and a differential pressure transducer connected to such pressure sensors for sensing the differential pressure caused by the sample introduced into one of the housings.

The differential pressure transducer provides an output indicative of the weight percent of sample remaining in suspension as a function of time and this output may be used for determining the weight fraction of the particulate solids passing any given mesh size, or the specific gravity of particulate material of known dry weight.

The invention will now be disclosed, by way of example, with reference to a preferred embodiment illustrated in the accompanying drawings in which:

FIG. 1 illustrates an embodiment of a sedimentation apparatus in accordance with the invention;

FIG. 2 illustrates an enlarged view of the top portion of one of the vertical housings of the apparatus;

FIG. 3 illustrates a section view taken along line 3—3 of FIG. 1;

Figure 6:
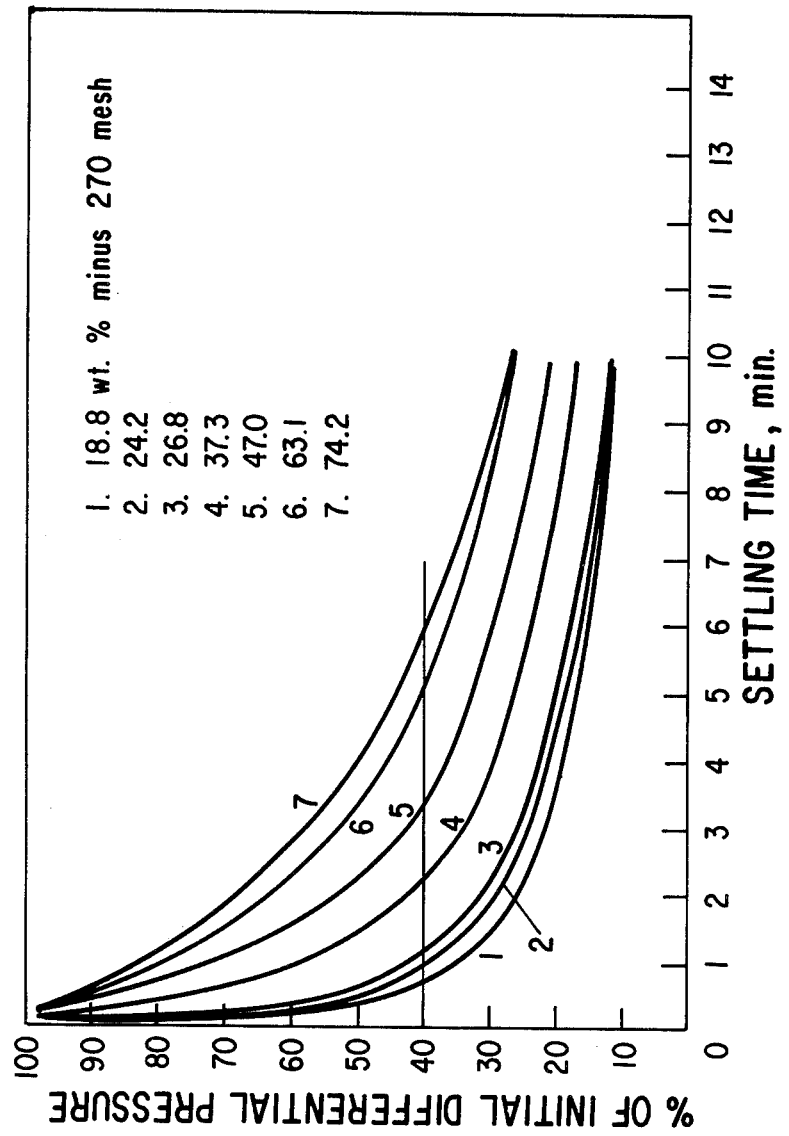
Figure 7:
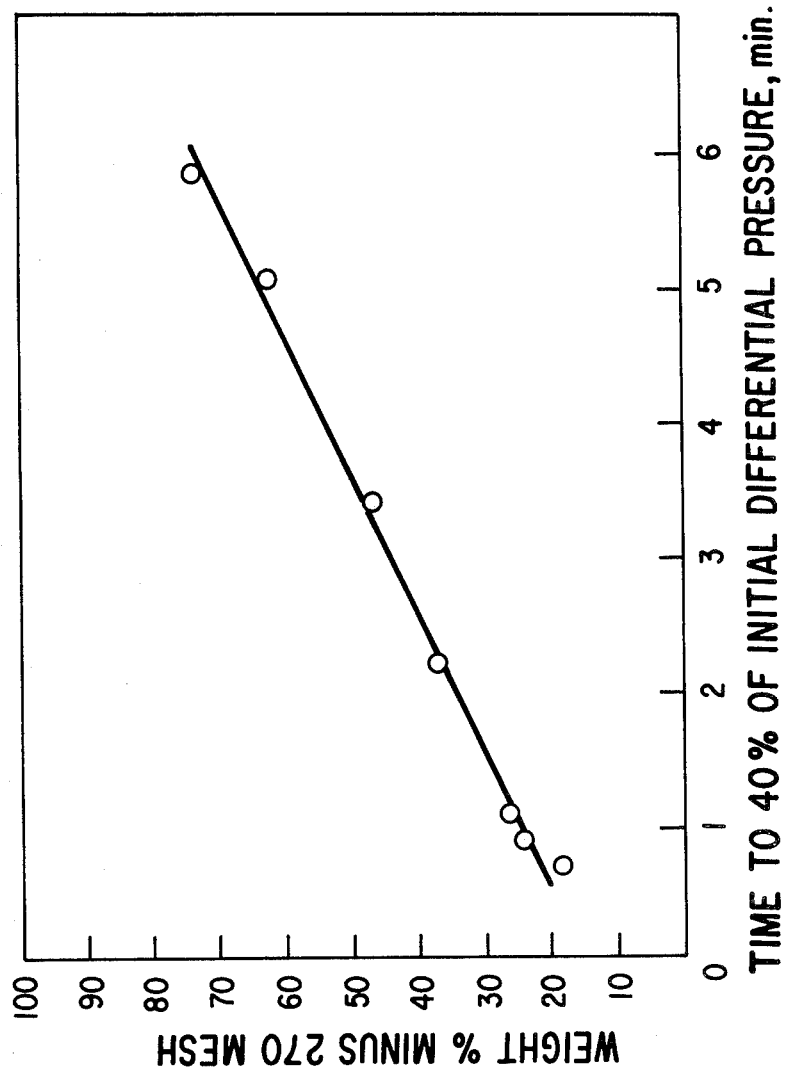

FIG. 6 illustrates the weight percent of various samples remaining in suspension at various times following introduction of the samples into the sedimentation apparatus; and FIG. 7 shows the linear relationship between the weight percent of a sample of a given size distribution, as determined by previous screen analysis, and the time required for the differential pressure to decrease to 40% of its initial value.

Referring to FIGS. 1-3, there is shown an embodiment of a sedimentation apparatus comprising two vertical housings 10 and 12 in the form of tubes having lower rectangular cross-sections 14 and 16, respectively. In the above embodiment, both tubes are made of plastic material such as Plexiglass (Trademark for a methyl acrylate plastic). Of course, the tubes could be made of metal or other suitable material. The tubes may be held in a vertical position in any conventional way, either resting on the floor or mounted on the wall. The tubes are held apart by spacers 18 and 20. The upper part of top spacer 20 is hollow and acts as a water bridge between tubes 10 and 12. Tube 10 is a reference tube and tube 12 is a settling tube or vice-versa and both tubes are initially filled with a reference liquid. In most applications, especially those dealing with measurements on finely ground ore, the preferred liquid used to fill the tubes 10 and 12 and the interconnecting bridge 20 is water. However, any suitable liquid less dense than the solids to be measured can be employed. The top of the tubes is provided with openings 22 within the bridge 20 to equalize the liquid level in both tubes. Partitions 24 are provided within the bridge 20 to damp any movement of liquid between the tubes, more particularly when a sample is introduced into the settling tube. Holes 25 are provided in the partitions to equalize the liquid level in the bridge and the tubes. The tubes 10 and 12 may advantageously be filled through an inlet 26 located at the bottom of the tubes and the level of water maintained through an overflow pipe 28 extending into bridge 20. The height, shape and cross-section of the tubes may vary and will, in some cases, depend on the particular application.

The particulate material is normally in suspension in water which is circulated continuously through a pipe 30, a funnel 32 and a drain pipe 34 connected to overflow pipe 28. Funnel 32 has a hole therein adapted to fit over the end of settling tube 12 and pipe 30 is movable as indicated by arrow A so as to direct the slurry containing the solid particles into the settling tube 12 when it is located on the left handside or directly through the output of funnel 32 when it is on the right handside for circulating the slurry.

A similar funnel 32 is positioned over the end of tube 10 and connected to overflow pipe 28 since the sample to be tested may equally be introduced into tube 10 and tube 12 used as a reference.

An insert 36 is placed into the top end of tubes 10 and/or 12 to direct the slurry below the level of the bridge so as to prevent the solid particles from getting into the bridge and possibly plug the holes 22 and 25. The lower end of the insert 36 has slots 38 as shown more clearly in FIG. 3 to allow the water portion of the slurry to rise into the bridge and equalize in both tubes.

An anti-splash device is placed over the end of the tube into which the slurry is introduced to prevent the solid materials in the slurry from creating too much turbulence in the measuring apparatus. The device consists of a funnel 40 having inwardly turned edges 42 and an inverted conical device 44 secured inside the funnel in such a way as to allow the slurry to flow down in a zig-zag manner as shown by arrow B in FIG. 2.

A pressure sensor 46 is mounted near the bottom of each tube. The pressure sensors are mounted on the same level so that the vertical distances between the top of the column of water in each tube and their respective pressure sensors are identical. Any form of pressure sensors can be used, the preferred device being a suitable flexible diaphragm mounted integrally on the flat portion of the lower end of each tube, or mounted independently inside the tube. The pressure sensors are connected to a differential pressure transducer 48 through tubes 50. Any commercially available transducer can be used to obtain an electrical output suitable for display, recording, or further data processing. The bottom of each tube is V-shaped and also provided with a drain 52 for flushing solid materials deposited at the bottom of the settling tube after test. The bottom of each tube is also slightly slanted so as to help flushing of the tubes through inlets 26 when the test is finished.

The apparatus disclosed above operates as follows:

Prior to adding a sample of particulate solids into settling tube 12, the differential pressure between sensors 46 is nil. Upon introduction of the sample, either as a dry or moist powder or as a slurry, into the liquid of settling tube 12, the differential pressure rises to a value proportional to the apparent weight of the solids in the liquid, which is proportional in turn to the dry weight of the sample in air, as indicated by the following equation:

$$R = K \frac{W(S_s - S_L)}{S_s} \quad (1)$$

$$R = K'W \quad (2)$$

where

R = differential pressure reading

K, K' = constants

W = weight of dry solids sample $S_s$ = specific gravity of solids $S_L$ = specific gravity of liquid (for water: $S_s > 1$)

The volume of water added with the solids and/or displaced by the solids is equally distributed among the two tubes through bridge 20 and does not affect the differential pressure. The initial reading persists until the settling particles begin to fall past the pressure sensors, at which time the differential pressure begins to decrease. If all the particles were allowed sufficient time to settle past the sensor, the differential pressure would return to zero. However, only sufficient time needs be allowed for predetermined weight fractions of the particles (expressed as a percentage of the initial differential pressure) to pass the pressure sensors 46 for an adequate reading to be made with the apparatus in accordance with the invention.

Figure 4:
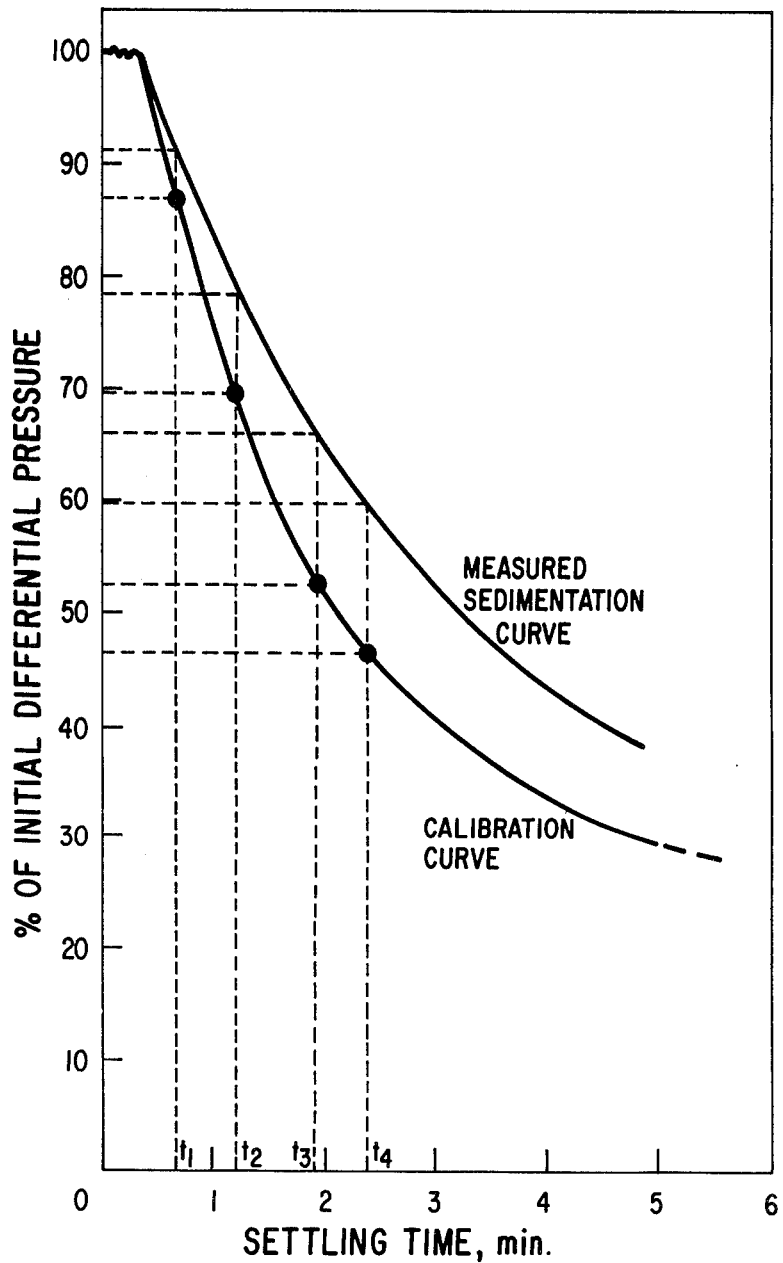
FIG. 4 illustrates the sedimentation curve of a sample of known size distribution used as a correlating parameter for determining the size distribution of a sample of unknown size distribution.

FIG. 4 illustrates the sedimentation curve (labelled) calibration curve) obtained from a sample having the following size distribution as previously determined by screen analyses:

86.9% −100 mesh
69.9% −200 mesh
53.1% −325 mesh
47.0% −400 mesh

The above sedimentation curve has been normalized so that the top of the characteristic corresponds to 100% of the initial differential pressure. Such sedimentation curve is used for calibrating the apparatus in accordance with the invention by finding the times $t_1$, $t_2$, $t_3$ and $t_4$ for settling each of the above weight fractions. Such times are used for determining the weight fraction passing the corresponding mesh size for any sample of unknown size distribution with the same specific gravity. For example, if the time $t_1$ for settling the −100 mesh size distribution of the calibration curve was 0.7 min. as read in FIG. 4, a corresponding time of 0.7 min. is read on the sedimentation curve of the sample of unknown size distribution (labelled measured sedimentation curve) and this will give a corresponding mesh size distribution of about 90.8% smaller than −100 mesh. The corresponding readings for times $t_2$, $t_3$, and $t_4$ will give about 78.8 wt. %−200, 66.0 wt. %−325 and 59.5 wt. %−400 for the size distribution of the sample of unknown size distribution. The above readings may be automatically provided by a suitable display device 54 under the control of a timer 56 operating at the above time intervals $t_1$, $t_2$, $t_3$ and $t_4$, as shown in FIG. 1.

Figure 5:
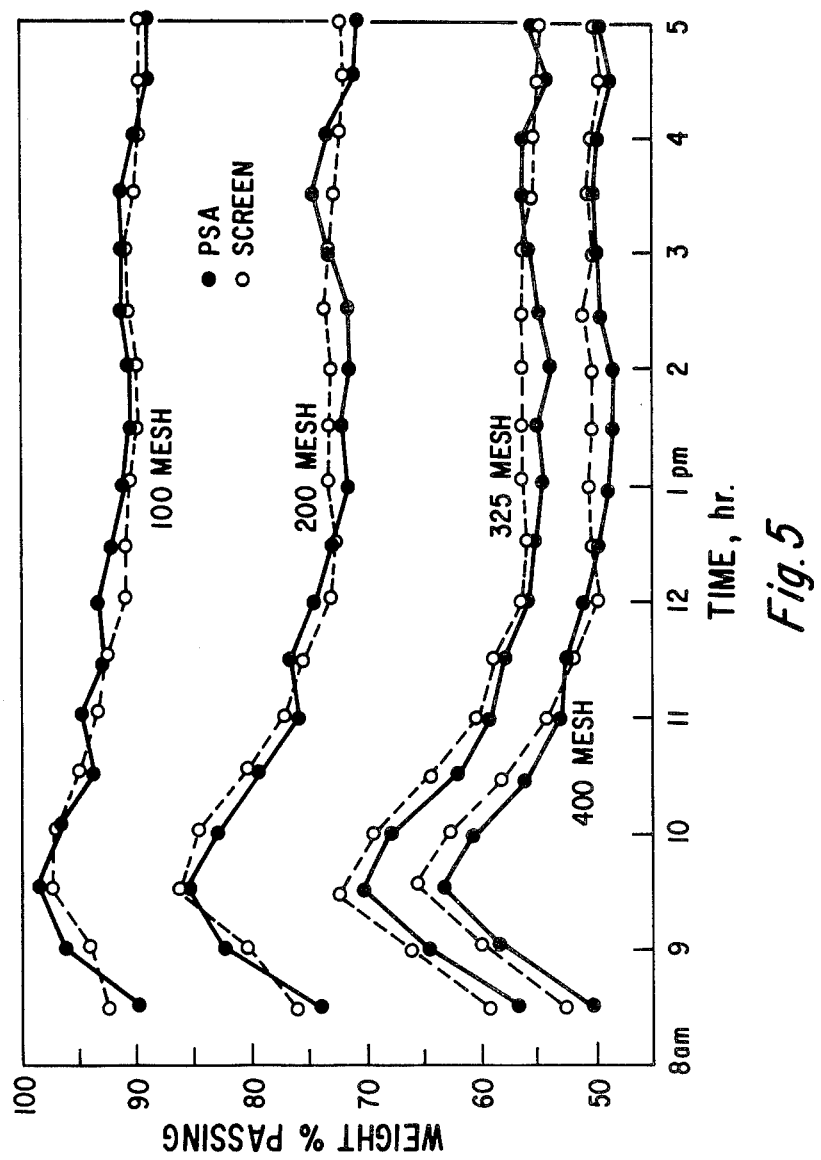
FIG. 5 shows a comparison between size distributions obtained by screening and from the apparatus in accordance with the invention for a series of samples of slurry taken at half hour intervals.

FIG. 5 shows a comparison between size distribution (wt. % passing 100, 200, 325 and 400 mesh) obtained by screening (dashed lines) and from the apparatus in accordance with the invention (solid lines) for a series of 18 pulp samples of slurry taken at ½-hr intervals in a concentrator. The readings agree within ±2–3 wt. %. The apparatus was calibrated using average data from 19 samples.

Other characteristics of the sedimentation curves could be used as correlating parameters for calibrating the apparatus. For example, referring to FIG. 6, sedimentation curves of various samples of known size distribution having different wt. %−270 mesh were obtained using the apparatus in accordance with the invention. From these curves, the relationship between the wt. % of −270 mesh material in the sample and the time required for the differential pressure to decrease to 40% of its initial value (i.e. 40 wt. % of sample remaining in suspension) was obtained by tracing a straight line at the 40 wt. % level as shown in FIG. 6. The values obtained were plotted in FIG. 7 and the time intervals were found to be linearly related to the weight fraction −270 mesh. This relationship was used to determine the weight % −270 mesh of any sample having the same specific gravity by noting the time taken to go down to 40% of initial differential pressure and reading the corresponding weight percent. For example, if it took 5 minutes for a sample of unknown size distribution to go down to 40% of initial pressure differential, then the weight % −270 mesh of that sample is about 63%. Other similar correlation characteristics may be derived from other known size distributions of the same sample and such characteristics used for calibrating the apparatus. Other characteristics of the sedimentation curves obtained with the apparatus in accordance with the invention could also be used as correlating parameters, for instance, the integral or differential of the curve at some point.

The particles can be removed from the measuring system by settling out on a fixed platform located above the pressure sensors rather than by being allowed to fall past the sensors as described above. However, in the latter case, the settled material can be readily flushed out of the apparatus when the apparatus is used to automatically measure the size distribution of a series of samples.

The apparatus of the present invention can also be used to measure the specific gravity of particulate solids, as indicated by consideration of equation 1 above. Thus, if the sample dry weight is fixed, the following relation for solids settling in water can be derived:

$$S_s = \frac{1}{1 - K''R} \qquad (3)$$

where $K''$ is a constant and the other symbols are as above.

The device of the present invention automatically provides a measure of the initial weight of the sample; the wt. % remaining in suspension or removed by settling at any time can therefore be readily calculated without any additional measurement. Moreover, the absolute weight of the sample is immaterial and need not be known explicitly. An advantage of the apparatus used to implement this novel method of making sedimentation measurements is the absence of moving parts or mechanical linkages. Furthermore, the apparatus is readily adaptable to semi-continuous operation whereby pulp samples can be processed automatically in rapid succession, at intervals of a few minutes.

Although the invention has been disclosed with reference to a preferred embodiment, it is to be understood that various modifications may be made to such embodiment and that the invention is not to be limited to the preferred embodiment. For example, any means, other than bridge 20, could be used for maintaining the same level of water in the two housings 10 and 12, such as drain holes located at the same level in both tubes. Other alternatives falling within the scope of the claims are also envisaged.

What is claimed is:

1. An apparatus for measuring the sedimentation characteristics of particulate solids comprising:
   (a) two separate vertical housings adapted to be filled with a liquid less dense than the particulate solids to be measured and a bridge interconnecting the two vertical housings adjacent the top thereof for communicating the two housings and so maintain the same level of liquid in the two housings;
   (b) means for introducing a sample of particulate solids to be measured in the top of one of said housings;
   (c) two pressure sensors located, at the same level, one in each housing; and
   (d) a differential pressure transducer connected to said pressure sensors for sensing the differential pressure caused by the sample introduced into one of the housings, said differential pressure transducer providing an output indicative of the weight percent of sample remaining in suspension above the pressure sensors as a function of time.

2. An apparatus as defined in claim 1, further comprising means for converting the output of said differential pressure transducer into an indication of weight fraction of the particulate solids passing any given mesh size.

3. An apparatus as defined in claim 2, wherein said converting means includes a display device connected to the output of said differential pressure transducer and a timer connected to said display device for energizing such display device at predetermined time intervals.

4. An apparatus as defined in claim 1, further comprising a display device connected to the output of said differential pressure transducer, said display device being calibrated to read directly the specific gravity of particulate material of known dry weight.

5. An apparatus as defined in claim 1, further comprising an inlet located near the bottom of each housing for filling the housings with said liquid, and an overflow located within said bridge for maintaining a constant level of the liquid in the two housings.

6. An apparatus as defined in claim 1, wherein the bottom of said housings is V-shaped and slightly slanted and provided with an outlet for flushing the solids deposited at the bottom.

7. An apparatus as defined in claim 1, further comprising a funnel secured to the top of the housing adapted to receive the sample of particulate solids and a tube mounted above said funnel and movable from a position right above the housing adapted to receive the sample to a position offset from said one position but still above the funnel for permitting continuous circulation of slurries containing the particulate solids with intermittent sampling at predetermined intervals.

8. An apparatus as defined in claim 1, further comprising an insert placed into the top end of said one housing to direct the slurry below the level of water in the housing.

9. An apparatus as defined in claim 1, further comprising an anti-splash device placed into the top end of said one housing for preventing the solid materials in the slurry from creating too much turbulence in the housing.

10. An apparatus as defined in claim 1, further comprising apertured vertical partitions located in said bridge for damping any movement of liquid between the two housings.

* * * * *